United States Patent [19]

Pallaroni et al.

[11] 4,326,574
[45] Apr. 27, 1982

[54] FLEXIBLE CONTAINER WITH VALVE

[75] Inventors: Francesco Pallaroni, Piacenza; Luciano Baldini, Grosio; Alberto Siccardi, Tirano, all of Italy

[73] Assignees: Safta S.p.A., Milan; Bieffe S.P.A., Grosotto, both of Italy

[21] Appl. No.: 100,978

[22] Filed: Dec. 6, 1979

[30] Foreign Application Priority Data

Dec. 18, 1978 [IT] Italy ................ 30940 A/78

[51] Int. Cl.$^3$ ............................................. B65D 30/24
[52] U.S. Cl. ....................................................... 150/8
[58] Field of Search ...................... 150/8, 9; 229/62.5; 206/438

[56] References Cited

U.S. PATENT DOCUMENTS 2,704,075 3/1955 Cherkin ................... 206/438 X
3,642,047 2/1972 Waage ......................... 150/8

Primary Examiner—Donald F. Norton
Attorney, Agent, or Firm—Holman & Stern

[57] ABSTRACT

A flat, flexible, sterilizable container for a liquid to be maintained and extracted under sterile conditions, said container comprising: a body having walls formed by a three-layer laminate including an outermost layer of a propylene polymer, an innermost layer of a copolymer of ethylene with a small amount of butylene, and an intermediate layer of an amide polymer; and a valve carried by said body comprising an elastomeric core whose spaced major faces are covered, one, by a three-layer laminate similar to said body wall forming laminate and, the other, by a two-layer laminate including a first layer of a copolymer of ethylene with little butylene and a second layer of an amide polymer.

18 Claims, 20 Drawing Figures

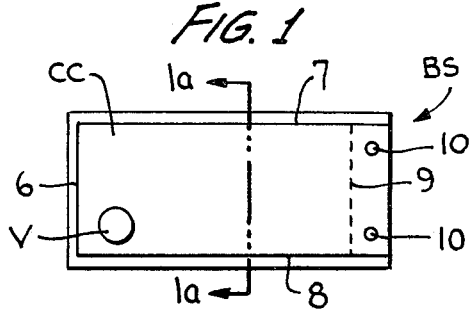
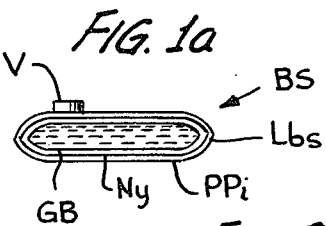
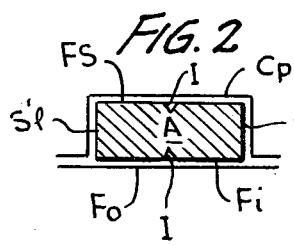
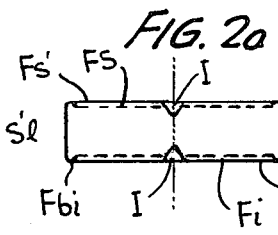
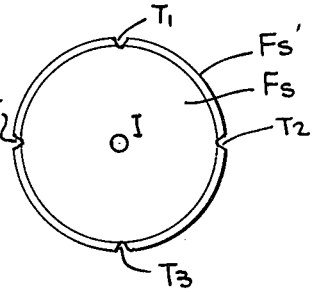
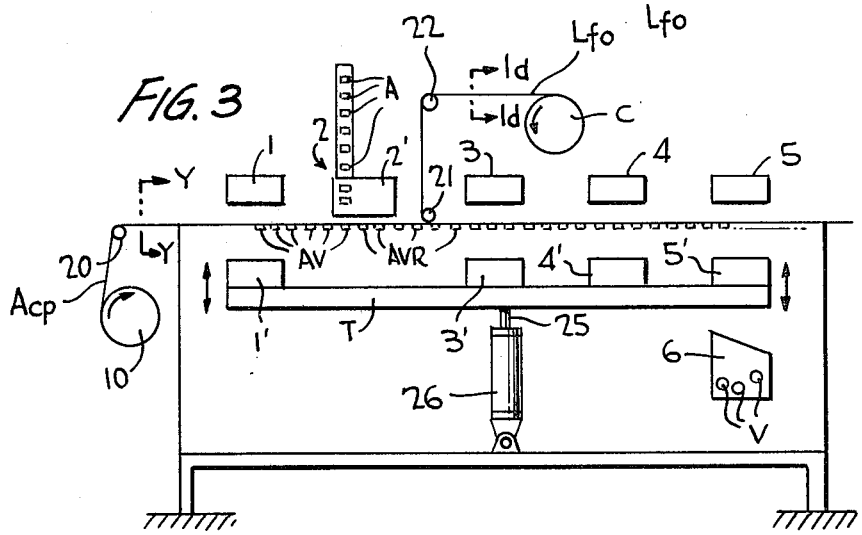
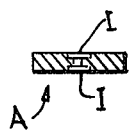

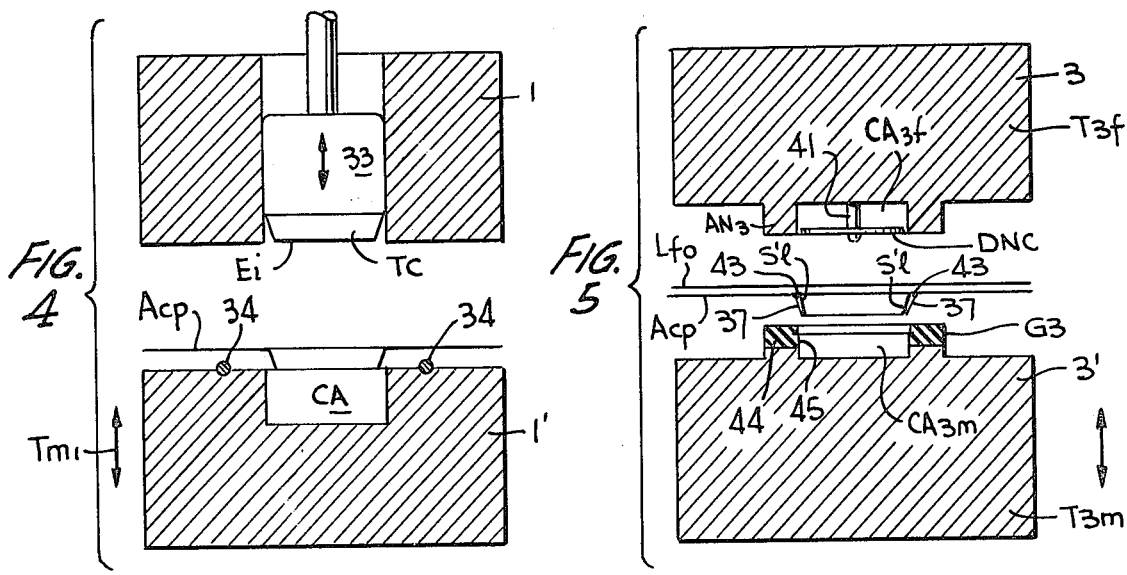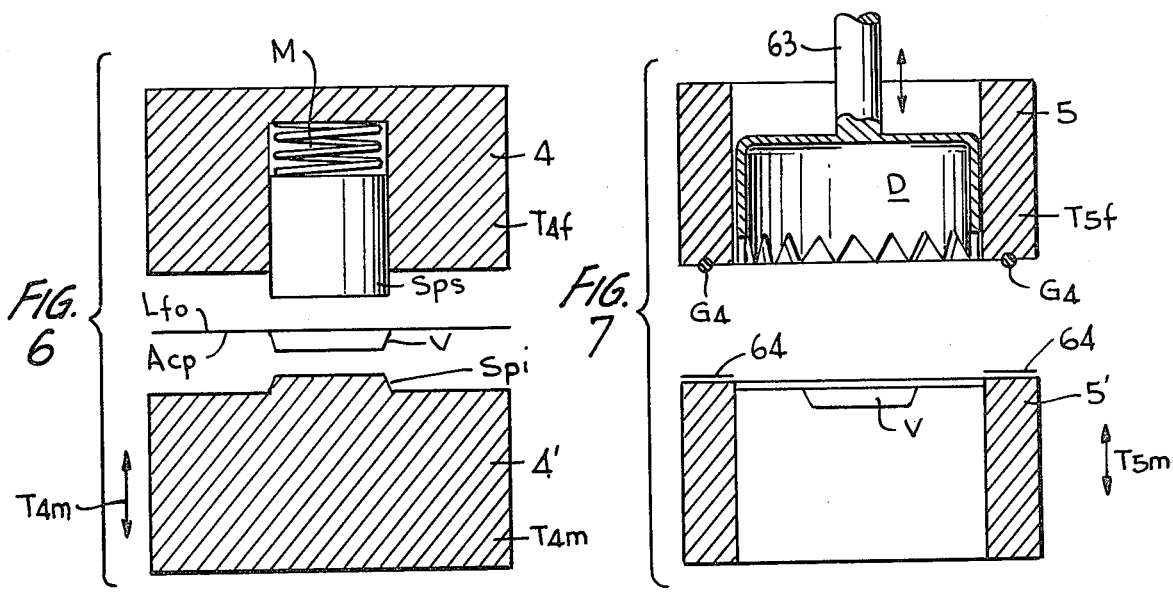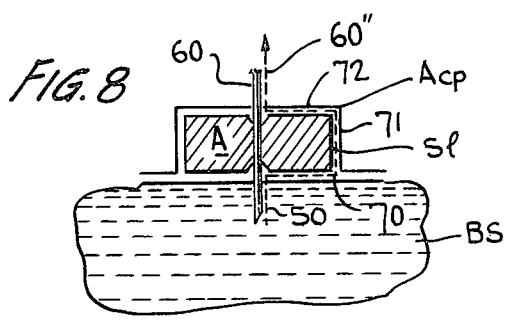

FLEXIBLE CONTAINER WITH VALVE

BACKGROUND OF THE INVENTION

1. Field of the Invention

The present invention relates to flexible flat containers made of substantially plastic material, sterilizable and capable of containing a liquid to be maintained and extracted under absolutely sterile conditions. These containers consist of a liquid containment body formed of walls made of material thermo-sealed on at least two sides, and of a valve element through which pointed means for removal of liquid can penetrate. This valve element may be made of a rubber piece coated with a plastic material.

2. Statement of the Prior Art

Flat flexible containers provided with an element for defluxion or liquid removal are already described in the technical literature. In particular, U.S. Pat. No. 2,704,075 describes flat flexible containers consisting of a containment body (an envelope or bag) constructed from tubular plastic material sealed at its ends, and of an element (e.g., rubber or plastic resilient material) which may be obtained as a continuous rib on the tubular containment body during extrusion, or applied by welding on the tubular containment body's wall. The element may be sealed in a plastic envelope made of PVC or polyethylene. The envelope containing the element has edges of the PVC or polyethylene protruding beyond the perimeter of said element. Generally, this last element is attached to the container or is kept sterile by a piece of Scotch tape which is removed at the moment of use.

The containers according to this prior (1952) patent have not, to date, had commercial success; in fact, the patented article has not been used on a commercial or even an experimental basis.

Containers similar to those of the above U.S. Patent are described in the French Patent Publication No. 2,186,402 (filed May 29, 1973, with the priority of May 30, 1972); here too, the indicated bag forming material is PVC or polyethylene. There are no examples of commercial application in the market place. The scarce commercial use of flat flexible containers in the field of sterile liquids, particularly of perfusion solutions, seems substantially due to problems with the indicated materials, PVC or polyethylene. Indeed, it is very difficult to make bags (with or without valves) which are sterilizable by common means (e.g., vapor) at temperatures above 110° C. Moreover, and especially with regard to PVC, contamination of the liquids contained in the bags by the decomposition products of the film-forming polymeric blend (above all, chloro-vinyl copolymer, plasticizer) is a persistent problem. Furthermore, PVC is highly permeable to water vapor and absorbs medicinal substances which renders it useless in many applications. Efforts to substitute film or sheets of PVC or polyethylene with films or laminates based on other polymers or copolymers (e.g., requiring substantially no plasticizers) have been severely limited not only in the very nature of these materials (none of which shows singularly the required combination of properties) but above all in the difficulty of providing them with a valve device satisfactorily fulfilling the three requirements of easy applicability, sure holding, and an absolute lack of contaminating decomposition products.

SUMMARY OF THE INVENTION

The primary object of the present invention is to provide a flat flexible container with a valve, which has none of the above-mentioned drawbacks, is effectively sterilizable and is free of any decomposition product.

Another object of the invention is to provide a bag for maintaining and drawing off liquids in absolutely sterile conditions, which can easily be provided with a valve puncturable by needles and cannulae so as to act as a liquid dispenser when perforated, and as a hermetic closure means when the perforating means is withdrawn. The containers according to the invention, having a structure of the type described in this introduction, are characterized in that the containment body is made of an envelope forming laminate $L_{bs}$ comprising: (1) at least a plastic film of polymers of ethylene with a small amount of butylene, and/or a film of propylene polymers, as well as a polyamide film; and (2) the rubber core of the valve element welded on the containment body wall is covered, on one of its major faces, by a laminate $L_{fo}$ consisting of: at least a film of polymers of ethylene with a small amount of butylene and/or a film of propylene polymers, as well as of a polyamide film; and, on the other major face, by a two-layer laminate, (Acp) comprising a film of a polymer of ethylene with a small amount of butylene and a polyamide film.

BRIEF SUMMARY OF THE DRAWINGS

FIG. 1 is a top view of the plastic solution containment bag and valve.

FIG. 1a is a cross-sectional view through the plastic solution bag and valve through plane (1a—1a of FIG. 1.

FIG. 2 is a cross-sectional view of the valve with associated plastic films.

FIG. 2x is a cross-sectional view of the two-layer laminate which forms the cover of the valve.

FIG. 2y is a cross-sectional view of the three-layer laminate which forms the bottom of the valve.

FIG. 2a is a side view of the elastomeric core of the valve.

FIG. 2b is a top view of the elastomeric valve.

FIG. 3 is a diagram of the apparatus used in the manufacture of the valve element.

FIG. 3a is a cross-section through the plane Y—Y of FIG. 3.

FIG. 3b is a cross-sectional view of the disc A which is an element of the valve.

FIG. 3c is a cross-section through the plane 1d—1d of FIG. 3.

FIG. 4 is a diagram of the die used to punch the pockets into the plastic film for formation of the valve.

FIG. 5 is a diagram of the die used for sealing the plastic film around the edges of the elastomeric core.

FIG. 6 is a diagram of the die used for bonding the plastic film to the upper and lower surfaces of the elastomeric core.

FIG. 7 is a diagram of the die used for cutting the fabricated valves from the plastic film.

FIG. 8 is a cross-sectional view of the completed valve punctured by a needle and shows a possible route of escape for the contained solution.

DESCRIPTION OF THE PREFERRED EMBODIMENTS

Figure 9:
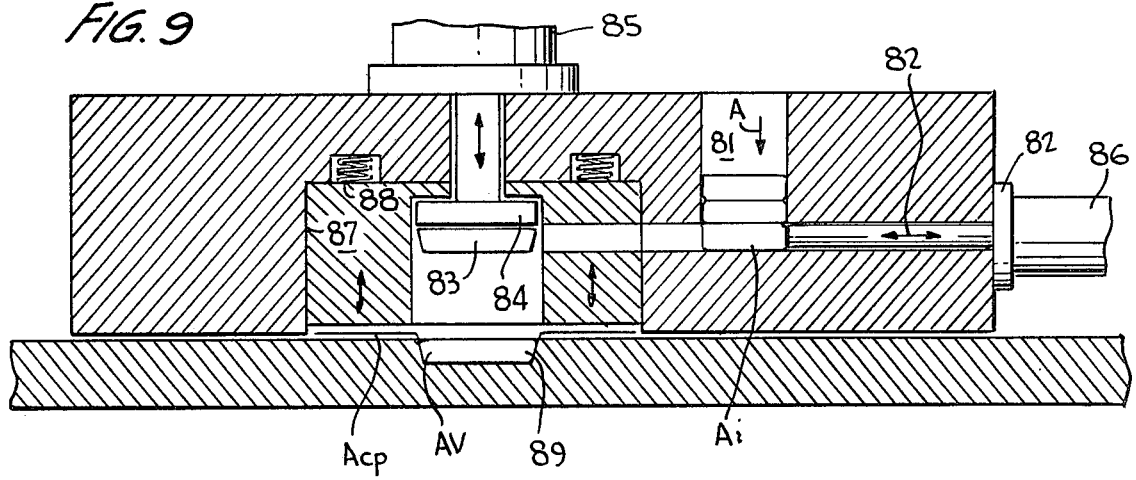
FIG. 9 is a diagram of the piston and cylinder apparatus which drives the moving dies used in the manufacture of the valves.

The various features and advantages of the invention are more clear from the following description of the preferred (but not limitative) embodiments described with reference to the attached drawings and examples. To briefly illustrate the ideas, FIGS. 1 and 1a show top views and a schematic cross-section respectively of a container or envelope BS according to the invention, comprising: (I) a liquid containment body CC which is formed of a laminate $L_{bs}$ (FIG. 1a) closed by transverse seals 6 and 9 (and possible longitudinal seals 7 and 8 when tubular film is not initially used); and (II) a dispensing valve V attached to CC. The envelope BS may have holes 10—10 for hanging on suspension hooks.

Components (I) and (II) have critical compositions and/or structures which are substantially described as follows:

(I) Liquid Containment Body CC of Bag BS

According to the invention, the liquid containment body consists of a bag-forming laminate $L_{bs}$ which as shown in FIG. 1a, comprises (proceeding from outside to inside):

(1) a film or layer $PP_1$ made of substantially isotactic macromolecules or propylene (alone or in combination with amounts below 10% of other monomers, e.g., olefins preferably ethylene); the thickness of this film ranges from 8 to 40μ preferably from 10 to 30μ, and is best around 20μ;

(2) a central film or layer Ny of amide polymers or copolymers, preferably polyamide-6 ("Nylon") having a thickness from 8 to 30μ and preferably from 10 to 25μ which may be biaxially oriented; and, (3) a film or layer GB made of copolymers of ethylene with minor amounts of butylene, in particular a film obtained by extrusion of the polymer sold by DuPont of Canada under the trademark "Sclair" and showing a thickness above 20μ and preferably from 20 to 90μ, most preferably 25 to 70μ.

(II) Valve V

The structure and composition of V, both critical for the invention, are shown in FIGS. 2, 2x and 2y. The valve consists of:

(1) a central core A;
(2) a cover Cp made of flexible two-layer film Acp, and
(3) a bottom Fo made of a flexible laminate $L_{fo}$ preferably having the same commposition as the bag-forming laminate $L_{bs}$. The core A is a parallelepiped (a small cylinder with a circular or elliptic cross-section, a truncate cone, a trapezoid and the like) and is defined by an upper face $F_s$, a lower face $F_i$ and a side surface Sl–S'l which is generally annular. The valve core of semi-rigid elastomeric material with elastic memory is preferably made by compression molding of a blend of butyl rubber and natural rubber (10 to 40%, preferably about 15% of natural rubber) to have good mechanical characteristics and keep fluid leakage within the limits allowed by the pharmacopoeiae.

In FIGS. 2a (front view) and 2b (top view), the preferred embodiment of the elastomeric core has a cylindrical shape and the following critical structural features:

(1) In the center of the top major surfaces $F_s$ and $F_i$ of disc A are two pre-puncturing conical indentation areas, I, having dimensions suitable for the most common hypodermic needles (60 in FIG. 8).

In an embodiment shown in FIG. 3b, A has a diameter of 20 mm and a thickness of 4 mm. The indentations, I, are depressions having a diameter of 2 mm and a depth of 1 mm resulting in a diaphragm 2 mm thick. With this structure of A, the introduction of the needle (60) is facilitated without reducing the tightness and the retention force of valve V.

(2) As can be seen from FIGS. 2a and 2b, the upper and lower faces $F_s$ and $F_i$ respectively have on their contours an annular rim or band $F_{bs}$ and $F_{bi}$, respectively, each having a peripheral edge Fs' and Fi' respectively, which project from the respective face bases $F_s$ and $F_i$.

(3) Several cuts, T, $T_1$, ... $T_2$ ... $T_n$ are made in the rims $F_{bs}$ and $F_{bi}$. Said cuts, which are not to be confused with the central identations I, can be more or less than four and have shape and size different from those of FIG. 2b.

As stated above, it has been found that the best elastic characteristics and the best leakage control are obtained by compression molding blends of natural and butyl rubbers (which may also contain conventional additives and vulcanizers). As is known in the art of compression molding, a small amount of silicone is put in the mold during manufacture of the cores. However, because of the composition and washing of the cores, A, to remove the silicone, the cores tend to stick to each other on their adjacent upper and planar surfaces ($F_s$ and $F_i$ respectively) when stacked in the loader or dispenser to be described below. By providing the cores A with the protruding edges $F_{bs}$(upper) and $F_{bi}$(lower) their contact area is minimized and the sticking or adhesive force becomes negligible over the weight of each core A so that the rubber cores fall and feed automatically. It has been found however, that the elimination of the sticking force by the edges $F_{bs}$ and $F_{bi}$ is accomplished by significant air penetration between cover Cp and flat surface $F_s$ as well as between bottom Fo and surface $F_i$. The cuts T, $T_1$, $T_2$, ... $T_n$ have proved themselves very efficient in confining the penetrated air to their small aperture where it remains and does not unglue the cover $C_p$ from $F_s$, nor the bottom Fo from $F_i$.

Cover $C_p$

According to a feature of the invention, the cover $C_p$ is made of a two-layer sheet Acp (FIG. 2x) consisting of a polyamide film Ny" and of a film $GB_1$ of ethylene $(C_2)$-butylene $(C_4)$ copolymer such as the "Sclair" of DuPont of Canada (in the following, indicated also as $C_2$–$C_4$ copolymer).

Bottom Fo

The bottom, Fo, consists of a laminate comprising an ethylene-butylene copolymer film $GB_2$, a central polyamide film Ny' and a propylene polymer film $PP_2$. The thickness of the $C_2$–$C_4$ copolymer films $GB_2$ in the laminate $L_{fo}$ and of $GB_1$ in the sheet Acp of cover $C_p$ are preferably equal to that of the corresponding film GB in the bag forming laminate $L_{bs}$.

It will be noted that in Acp and $L_{fo}$, said $C_2$–$C_4$ copolymer films $GB_1$ and $GB_2$ are both internal and are heat-sealed to each other along the edges B—B' (FIG. 2).

In an embodiment of the invention the laminate $L_{bs}$ was also used as laminate $L_{fo}$ and the film thicknesses were the following: $PP_1 = PP_2 = 20\mu$; $GB = GB_2 = 50\mu$; $Ny = N'y = 15\mu$.

In Acp, $GB_1$ had a thickness of $50\mu$ while that of N"y was $20\mu$.

Valve Preparation

The valves V, according to the invention, are prepared independently from the preparation of the bags BS. Valve preparation is described with respect to the machine depicted in FIGS. 3 to 7.

In FIG. 3 (front schematic partial view) only the essential and characterizing parts of the valve forming device are shown, the conventional parts thereof being purposely omitted for clarity's sake.

Numeral 10 in FIG. 3 indicates a bobbin. The sheet Acp is shown in cross-section along plane Y in FIG. 3a. Sheet Acp is obtained by coupling a polyamide-6 film N"y (FIGS. 2 and 3a) having a thickness of $20\mu$ with a $50\mu$ thick film, $GB_1$, of ethylene-butylene copolymer (Du Pont's "Sclair"). The coupling takes place by coating preferably on N"y a 2 gr/m² layer of a polyurethane adhesive.

The sheet Acp which unwinds from bobbin 10 and is stretched by roll 20, passes on a head 1–1' which forms empty pockets AV in Acp. Forming head 1–1' consists of a stationary part 1 and a mobile part 1' which, by moving towards and contacting 1, cold-punches for less than one second (e.g., for a half second) the surface of Acp and forms therein empty pockets AV having dimensions corresponding to those of the rubber cores A. The punching time must be long enough to delete the elastic memory of sheet Acp so that the form of pockets AV will be maintained. The punching time, however, must not be so fast that the sheet Acp shears and interrupts the operation of the machine. The pockets AV so obtained pass under a loader 2 provided with a positioning element 2' through which the cores A piled in 2 fall at the right moment in the correct position inside the pockets AV. The pockets have a diameter slightly greater than that of discs A; e.g., if the diameter of A is 20 mm, that of AV is 20.5 mm, at an equal height of 4 mm. The pockets filled with cores, indicated as AV.R, go under a roll 21 which in cooperation with roll 22, pulls under tension in the same advancing direction of AV.R the bottom forming laminate $L_{fo}$, unwinding it from bobbin C. A cross-section of $L_{fo}$ in the plane of 1d (FIG. 3c), shows that it consists of a $C_2$–$C_4$ copolymer film $GB_2$ ($50\mu$ thick) of a $15\mu$ thick polyamide film N'y and of $20\mu$ thick film $PP_2$ of polypropylene, possibly containing a small amount of combined ethylene units (EP). The welding head 3–3' heat-seals $L_{fo}$ to Acp along the circular crown B–B' (FIG. 2), followed by a bonding head 4–4' and a cutting or shearing head 5–5' from which the finished valves V exit and fall into the collector 6. All stations, namely the pocket forming station 1–1', the heat-sealing station 3–3', the bonding station 4–4' and the shearing station 5–5', consist of a stationary section (1, 3, 4 and 5) and of a mobile section (1', 3', 4' and 5'). These last are associated with a moving crossbar T which brings them into contact with the stationary parts 1, 3, 4 and 5 by the movement of a piston 25 moving in a pneumatic cylinder 26.

The structural and functional details of these stations are schematically shown in the FIGS. 4 to 7.

FIG. 4 shows the pocket forming head 1–1' of FIG. 3. It consists of the upper stationary head $T_{f1}$ in which slides a shaped cylinder 33 whose lower portion TC is a truncate cone having a smaller base at the lower end Ei of a diameter equal to that of the valve core A. The valve core A, in a preferred embodiment, is likewise slightly conical, e.g., the upper face $F_s$ is wider by a few tenths of a millimeter, than the lower face or vice versa; if $F_i$ is 20 mm wide, the other face $F_s$ will be 19.80 mm wide.

The mobile head $T_{m1}$ shows a cavity CA which could have the same dimensions as the pocket AV so that the lowering of the forming cylinder 33 causes the correct formation of pocket AV in Acp. It has, however, been found advantageous to determine the pocket depth by controlling exclusively the downstroke of cylinder 33. The rubber circular gasket 34 which surrounds cavity CA and protrudes slightly beyond the upper surface $S_3$ serves to hold the sheet Acp during its deformation operation.

FIG. 5 shows an advantageous embodiment of the welding head 3–3' whose upper stationary heated portion $T_{3f}$ has a cavity $CA_{3f}$ with a pin 41 on which a small disc DNC made of non-heat conductive material is placed; in the lower mobile head portion T3m (not heated) a second cavity $CA_{3m}$ is present in whose outer ring is inserted a rubber gasket $G_3$ which is sufficiently elastic and very heat resistant. $CA_{3m}$ has critical dimensions in that its diameter and height correspond to the diameter and height of the core A and the sum of the dimensions of Acp, $L_{fo}$ and the tolerance admitted in the machine advancement. With the combination of these two measures (small disc DNC in $CA_{3f}$, and critical dimensions of $CA_{3m}$), the following essential results are obtained. When $CA_{3m}$ moves upwards, it will initially puch Acp against $L_{fo}$, then $L_{fo}$ against the stationary disc DNC which will push $L_{fo}$ back against Acp and the core A, and so expel the air still present inside the pocket AV. The $CA_{3m}$ seat having dimensions exactly corresponding to the sum of the dimensions of core A, of the thicknesses of the Acp and $L_{fo}$, and of the advancement tolerance, pushes the Acp sides 37 against the lateral surface $S_l$–$S'_l$ of A expelling thus the air present in the small (triangular) gaps 43. At the same time the welding circular crown $G_3$ (made of "TEFLON" or of other thermoresistant material), is so that its inner sides 44 are extremely close (near) to the vertical sides 45 of $CA_{3m}$, thereby expelling further air and welding the Acp at the nearest possible point along the base Fi and the side $S_l$–$S'_l$, of valvular core A. Indeed a major problem in the preparation of valves is the curling of Acp (which is lighter) on A and from the presence of air (e.g., in 43) which renders partially useless the successive sterilization and more complicated the successive bonding of Acp and $F_{fo}$ to A. With the practice of the invention, i.e., use of a core A having edges F's and F'i slightly protruding, and cuts in $T_1, T_2 \ldots T_n$ (air vents), use of a cavity $CA_{3m}$ having the dimensions of the covered core plus the tolerance, use of a welding gasket $G_3$ practically aligned with $CA_{3m}$ and use of a disc DNC controlled by 41, a valve V in which potentially trapped air unglues neither Acp nor $L_{fo}$ from A and therefore does not pollute the system is obtained. The welding gasket $G_3$ corresponds to the protruding annular portion $AN_3$ on $CA_{3f}$, which determines the crown width B–B' of FIG. 2 on which $L_{fo}$ and Acp are heat-sealed to each other.

To prevent escape of liquid 50 from the bag GS along the indicated dotted line in FIG. 8 when the core is punctured by a needle 60, (i.e., along the lower part 60' of needle 60 and the path sections 70-71-72 along the faces $F_l$, $S_l$ and $F_s$ respectively of core A within the valve V, and then along the upper part 60'' of needle 60 out of cap Acp), it is necessary to bond A both to $L_{fo}$ and Acp along the major flat faces $F_s$ and $F_i$ (FIG. 2).

FIG. 6 shows the bonding head 4-4' of FIG. 3, which consists of two heads, an upper stationary head $T_{4f}$ and a lower movable head $T_{4m}$ both heated at e.g. 160°-170° C.; preferably one of the two heads, more preferably the upper stationary head $T_{4f}$ which has to bond $L_{fo}$ i.e., the thicker laminate to $F_i$ of A, is at a temperature higher than that of $T_{4m}$, e.g., $T_{4f}$ is at 170° C. and $T_{4m}$ at 130° C. The two heads have the projections $S_{pi}$ on $T_{4m}$ and $S_{ps}$ on $T_{4m}$ so sized that only the faces $F_s$ and $F_i$ of core A are involved thus limiting the area od $L_{fo}$ and Acp circumscribed within the edge B–B', already sealed.

This serves to avoid an excessive deformation and a further heating of the bonded films; indeed the circular area of the welded films B–B' must then be cut and this shearing is difficult if said circular area is warm. Further, as the core thicknesses are never exactly constant and vary 2 to 3 thousandths of a millimeter from one core to the other, it has been noticed that the adhesive forming action varies because of the core thickness variation, even when the pressure exerted by Sps and Spi is equal. (The temperature plays no important role as it is near or under the film melting points). To get conditions of constant charge by the projections Sps and Spi on the faces to stick (on which faces the distributed charge varies with the variation of the thickness of A), a spring is inserted in the bottom of projection Sps whereby Sps is slightly mobile, i.e., shows a given play determined by the spring whose tension can be controlled by a screw not shown. The spring characteristics are such that a constant charge is obtained on the faces of films $L_{fo}$ and Acp, as wide as the faces $F_s$ and $F_i$ of A, at varying thicknesses of A. FIG. 7 shows the shearing head 5-5' of FIG. 3, consisting of an upper head $T_{5f}$ which is a circular, toothed, mobile hollow punch, of a lower head $T_{5m}$ also mobile, of a film cutter 64 and of a piston 63 for the toothed hollow punch D of $T_{5f}$. Its width is for example 30 mm (20 mm of the core A diameter, 10 mm of the circular area B–B' to weld $L_{fo}$ to $L_{bs}$); this width is slightly lower than that width which the welding head $G_3$ has welded Acp to $L_{fo}$, which width is for example 32 mm (20 mm of the core and 6 mm on each side of the same core).

The width of the punch $T_{5f}$ which can be for example 30 mm (necessarily less than the 32 mm of the welding head) insures that the shearing occurs on the portion of films welded to each other. The punch is toothed (D) and cuts through by action of the teeth D and the fall speed. The sheared valves V fall within $T_{5m}$ and are collected in the bin 6 of FIG. 3.

FIG. 9 is a schematic view of the core loader 2 of FIG. 3. It consists of a container 81 of cores A, the lowest of which goes to a positioning sledge 82 in the position 83 under the pressing-positioning disc 84 activated by the piston 85. In the first part of its downstroke, disc 84 frees the pressor 87 which under the pressure of a spring 88 presses and keeps under tension the two-layer film Acp already provided with pockets AV; in the continuation of its stroke, disc 84 inserts into the pocket AV the small core 83, leaving it in the position 89. After that the sledge 82, under the action of piston 86, brings the lower disc Ai to the position 83, returns back and is ready for another cycle starting just after the pressing disc 84 has brought rubber 83 to position 89. The stack of rubber cores can obviously be substituted with a series of cores assembled on a roll canal which is inclined and offers to the sledge 82 a series of rubbers disposed on a horizontal plane. As previously stated, cores A show a circular edge F's and F'i which is for example 1 mm high when the rubbers have for example a diameter of 20 mm and a height of 4 mm.

Figure 11:
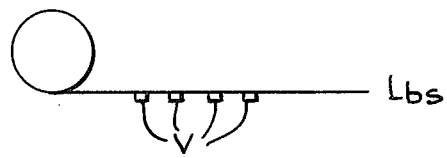
FIG. 11 shows the valve V sealed to the outer wall of laminate $L_{bs}$.
Figure 12:
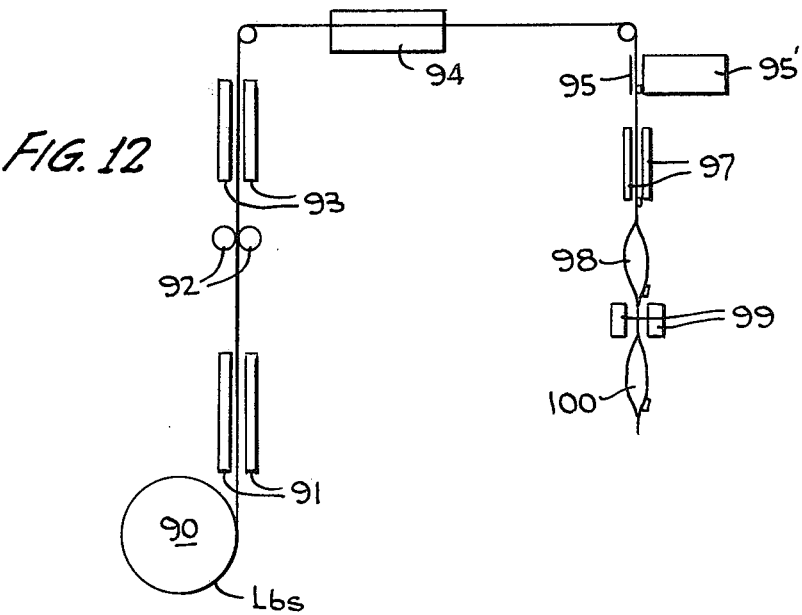
FIG. 12 is a schematic flow sheet of the "form and fill" process with the inventive step of sealing the valves V to the laminate $L_{bs}$ included.

With the above device it is possible to make valves V to be bonded to an inner wall (FIG. 10) or outer wall (FIG. 11) of the bag $L_{bs}$ forming laminate. This bonding can be carried out with conventional means. FIG. 12 shows schematically the "form and fill" process to produce and fill the valved bags of FIG. 1. From the bobbin 90 a laminate $L_{bs}$ is unwound, washed in a reservoir 91 containing a polyphosphate solution of ionized water and then pressed between rubber rolls 92; it is dried and sterilized with UV rays in a dryer and sterilizer 93, then is folded by folding means 94, is provided with valves V in a welding step, said valves 95 coming from the store 95', goes through the longitudinal welding bar 97, is filled with liquid by a filling means 98, is transversely welded and cut in bags by a welding bar and cutting means 99. The product falls into a bin 100 in the form of bags sealed on the four sides, provided with valves and filled with liquid.

The bags filled with liquid are sterilized preferably at 116° C. for about 40 minutes; it has been noted that during the sterilization procedure the filled bag shrinks less than 6% in a range of about 4 to 5%. This shrinkage has beneficial effects on both the aesthetic and mechanical characteristics. Indeed the sterilized filled bags are more completely filled than non-sterilized bags and therefore have a better appearance. Furthermore, the heat-shrinkage not only stresses the bag seals, thus testing their resistance, but also completes the welding of the valve on the bag by eliminating possible air pockets and better and more completely fixing the valve to the bag body. Accordingly, the sterilized bags have better appearance and strength compared to the unsterilized containers. This sterilization not only improves the characteristics of the bag but is also a quality control test. Indeed further conventional quality control steps become superfluous because, as it has been found in practice, only the 100% safe bags withstand the sterilization procedure and those bags which withstand sterilization pass any other, even very severe control tests.

The following non-limiting examples further serve to illustrate the invention:

EXAMPLE 1

(A) Small discs A having diameter of 20 mm, height of 4 mm, a projecting edge of 1 mm, two central indentations I with a diameter of 2 mm and a depth of 1 mm and four cuts T, $T_1$, $T_2$, $T_3$ of 1 mm were prepared by compression molding of a blend of natural rubber with 30% butyl rubber. The discs, which were identical on each side to avoid orientation problems, were washed with a polyphosphate solution and ionized water.

(B) A two-layer laminate Acp was prepared by combining a 50μ thick ethylene-butylene copolymer film $GB_1$ with a 20μ thick unoriented polyamide-6 film (N″y) coated with a 2 gr/m² polyurethane adhesive layer.

(C) A three-layer laminate $L_{fo}$ was prepared consisting of a 50μ thick ethylene-butylene copolymer (GB₂), of a 15μ thick polyamide-6 central film (N′y) coated on both sides with a 3 gr/m² adhesive layer of two polyurethane components and of a 20μ thick film of polypropylene containing 4% ethylene combined units.

(D) Laminate $L_{fo}$ was used as bag-forming laminate $L_{bs}$. In the above laminates the ethylene-butylene copolymer films were those obtained by extruding the polymers sold by Du Pont of Canada under the trademark "Sclair", the polyamide-6 films were those sold under the trademark "Filmon Bx" by Snia Viscosa and the film in copolymers of propylene alone or with little ethylene (EP) where those sold by Moplefan S.P.A.

The machine of FIG. 3 was supplied with the two-layer laminate Acp described in paragraph (B) above, with rubber discs as in (A) and with the three-layer laminate of paragraph (C). At the exit of this machine having the forming-, welding, bonding- and cutting-heads of FIG. 3, valves V were obtained which were submitted to the following tests.

Sterilization

The valves were subjected to a vacuum up to 600 mm Hg and were sterilized with ethylene oxide for 12 hours at 40° C. under 1.8 atm. The valves then underwent vapor sterilization at 118° C. for 30 minutes under a counterpressure during cooling of 1.1 atm.

Puncturability (DIN 58 363)

Figure 10:
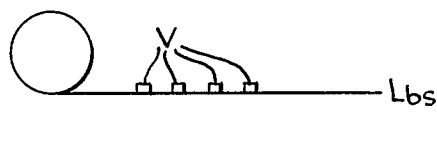
FIG. 10 shows the valve V sealed to the inner wall of laminate $L_{bs}$.

The puncture force with a needle amounts to 4 kg. The tested valves were sealed to the outer wall (FIG. 11) of a bag forming laminate $L_{bs}$ having the composition of $L_{fo}$ described in paragraph (C) above. (FIG. 10 shows the case in which the valves V are sealed to the inner wall of $L_{bs}$.)

This laminate $L_{bs}$ was subjected to the "form and fill" process of FIG. 12 in which bags of 14×35.5 cm filled with a liter of perfusion solution were prepared by submitting the laminate $L_{bs}$ from roll 90 to a washing step 91, to a squeezing of the washed laminate between rolls 92, to a drying and UV sterilization in oven 93 and to a folding means 94; a valve V, falling from the valve dispenser 95' (which can be the valve store 6 of FIG. 3), is sealed in 95 to the inner (FIG. 10) or outer (FIG. 11) wall of the folded laminate which is then longitudinally welded by the bars 97 to form a bag open only on one end through which the perfusional liquid is introduced therein (step 98).

This open end or mouth of the filled bag is then closed by bars 99 which make the transversal weld on said mouth and at the same time separate the filled bag from the last and/or successive one. The valved closed bags are stored in bin 100. Each step of the "form and fill" process is generally well known, and FIG. 12 shows them only in a schematic way while the valve application step 95 according to the invention is carried out as in FIG. 3. The filled bags so obtained are further submitted to the following tests.

Water-Tightness

For this test, filled and sterilized valved bags were used.

the valve was punctured with a "defluxion organ" (dispenser), and clamp closed: no less was registered in 10 h.

the valved bag was heavily mistreated, repeatedly folded until the protection two-layer laminate was wrinkled (without, however, ungluing), then punctured with a needle and clamped closed: no less was noted in 10 h.

the valve was punctured ten times with a needle having a diameter of 0.9 mm and then the bag was hung with no loss resulting.

even with repeated punctures and extractions with defluxion means as well as with the needle, the two-layer laminate has numerous holes in the puncture area but does not unglue from the rubber around such an area.

by puncturing the valve with the defluxor and immediately extracting it, the rubber re-closes automatically; by leaving the defluxion means in the rubber for periods of 25 minutes, the re-closure is no longer immediate and complete.

Defluxion

The valve was placed at a point about 15 mm above the bag bottom weld thereby the defluxer penetration point was at about 25 mm thereabove.

Although the discharge point is not on the bag bottom, the bag is practically emptied completely since the bag parts adhere to one another as the bag empties; the volume of residual liquid is from 1 to 3 ml, i.e., is comparable to that left in a glass bottle.

Defluxer retention force (DIN rule 58363)

A weight of 1 kg×5 h was applied to a tag inserted into the valve without causing the tag to detach. The DIN rules require a mass of 0.5 kg×5 h.

EXAMPLE 2

Rubber valves V, a two-layer laminate Acp and a three-layer laminate $L_{fo}$ as described in the above paragraphs (A), (B) and (C) respectively, were used with the only difference that the film GB₂ had a thickness of 40μ. Results comparable to those of Example 1 were obtained.

EXAMPLES 3 TO 5

Tests were carried out to find the best compositions of the films GB, GB₁ and GB₂ consisting of polymers of ethylene with a minor amount of butylene, according to the thermo-mechanical stress to which the bag is submitted. It has been found that:

(I) With thickness of GB, GB₁ and GB₂ lower than 30μ, it is advantageous to add to the polymer (bSclair") a small amount, e.g., from 0.01 to 0.2% of a wetting agent chosen for example between the hydrogenated fats and the related amides (in particular hydrogenated ricin oil, eucamide and the like).

(II) When the melting point is to be lowered and the film thickness is below 40μ, it is convenient to add to the polymer a wetting agent as in (I) but together with a corresponding amount of ethylene-vinylacetate copolymer (EVA).

(III) When it is desired to increase the melting point, the tenacity (and thus the tensile strength especially of the film GB in the bag forming laminate ($L_{bs}$), the chemical resistance and the impermeability to $O_2$ and $H_2O$, it is preferred to use a blend made of a low density (0192) "Sclair" polymer with a medium high density (e.g., 0.95–0.96) "Sclair" polymer. These low, medium and high density polymers are commercially available. The higher the tenacity of the desired film, the higher the amount in the blend of the high density polymer.

Obviously the invention has been described for clarity's sake with reference to the drawings and examples but is not limited to these embodiments as it is susceptible of changes and modifications which, being within the reach of the person ordinarily skilled in the art, fall naturally within the spirit and scope of the following claims:

We claim:

1. A flat, flexible, sterilizable container capable of sterilely containing a liquid to be removed under absolutely sterile conditions, said container comprising a body portion having walls sealed on at least two sides and defining therebetween a liquid receiving and maintaining compartment, and a valve carried by said body portion and being penetratable by pointed instruments to provide access to liquid within the compartment:

said body portion walls comprising a first section of a three-layer laminate including:
(1) an outermost layer comprising a major proportion of a propylene polymer;
(2) an innermost layer comprising a copolymer of ethylene with a minor proportion of butylene; and
(3) an intermediate layer of an amide plymer; said valve comprising an elastomeric core having spaced major faces, said major faces being joined by sides, said core being covered on one of said faces by a second section of said three-layer laminate and the other of said faces being covered by a two-layer laminate including:
(a) a first layer comprising a copolymer of ethylene with a minor proportion of butylene; and
(b) a second layer comprising an amide polymer;
said two-layer laminate and said second section of said three-layer laminate covering said core of said valve being sealed to each other and said valve being sealed to a wall of said body portion.

2. The container of claim 1, wherein said amide polymer is biaxially oriented.

3. The container of claim 1, wherein said amide polymer film is polyamide-6.

4. The container of claim 1, wherein said layers containing said amide polymer are adhesively bound to said innermost layer and said outermost layer of said three-layer laminate and to said layer of said two-layer laminate.

5. The container of claim 4, wherein said adhesive is polyurethane.

6. The container of claim 1, wherein said elastomeric core is a blend of butyl rubber and natural rubber.

7. The container of claim 6, wherein said blend comprises natural rubber in a range of about 10% to about 40%.

8. The container of claim 7, wherein said blend is about 15% natural rubber.

9. The container of claim 1, wherein said outermost layer is a homopolymer of propylene.

10. The container of claim 1, wherein said outermost layer is a copolymer of at least 90% propylene.

11. The container of claim 10, wherein said outermost layer is a copolymer of propylene and ethylene.

12. The container of claim 1, wherein each of said major faces of said core has a peripheral annular rim projecting from said major face.

13. The container of claim 12, wherein said sides have a multiplicity of gaps.

14. The container of claim 1, wherein each face of said core has a centrally located indentation.

15. The container of claim 1, wherein said propylene polymer layer is in a range of about $8\mu$ to about $40\mu$ thick, said amide polymer layer is about $8\mu$ to about $30\mu$ thick, and said ethylene-butylene copolymer layer is in a range of about $20\mu$ to $90\mu$ thick.

16. The container of claim 15, wherein said polypropylene polymer layer is in a range of about $10\mu$ to about $30\mu$ thick, said amide polymer layer is in a range of about $10\mu$ to about $25\mu$ thick and said ethylene-butylene copolymer layer is in a range of about $25\mu$ to about $30\mu$ thick.

17. The container of claim 16, wherein said polypropylene polymer layer is about $20\mu$ and said amide polymer layer is about $15\mu$ thick and said ethylene-butylene copolymer layer is about $50\mu$ thick.

18. The container of claim 1, wherein said two-layer laminate has a pocket and said core is in said pocket.

* * * * *